United States Patent [19]

Anderson et al.

[11] Patent Number: 4,929,769
[45] Date of Patent: May 29, 1990

[54] NOVEL POLYETHER CONTAINING AT LEAST ONE 2-HALOMETHYLOXYETHYLENE UNIT AND 2,3-DIHYDROXYPROPYL END GROUPS

[75] Inventors: Norman S. Anderson; Albert L. Promislow, both of Charlotte, N.C.; Randy L. Rayborn, Winder, Ga.; Rastko Vukov, Mississauga, Canada

[73] Assignees: Hoechst Celanese Corporation, Somerville, N.J.; Alkaril Chemicals, Inc., Ontario, Canada

[21] Appl. No.: 344,598

[22] Filed: Apr. 28, 1989

[51] Int. Cl.$^5$ .............................................. C07C 43/11
[52] U.S. Cl. .................................. 568/614; 568/613; 568/674; 568/675
[58] Field of Search ............... 568/675, 681, 614, 613, 568/674

[56] References Cited

U.S. PATENT DOCUMENTS

| | | | |
|---|---|---|---|
| 4,001,141 | 1/1977 | Kalupissis et al. | 568/614 |
| 4,072,638 | 2/1978 | Boulet et al. | 568/614 |
| 4,173,710 | 11/1979 | Boulet et al. | 568/614 |
| 4,576,967 | 3/1986 | Urata et al. | 568/675 |

Primary Examiner—Werren B. Lone
Attorney, Agent, or Firm—Forrest D. Stine

[57] ABSTRACT

A halogenated polyether is provided having a chemical structure which has been found to possess the requisite characteristics for satisfactory service as a promoter of good adhesion between a polymeric surface (e.g., a polyethylene terephthalate tire cord) and an elastomeric material (e.g., rubber). The halogenated polyether may be formed by (1) the reaction of an organic polyhydroxy compound with epihalohydrin (e.g., epichlorohydrin) to create ether linkages, (2) the epoxidation of the ends of the ether chains which extend from the residual portion of the organic polyhydroxy compound, and (3) the substantial hydrolysis of the epoxy groups (as described). The resulting halogenated polyether is substantially free of epoxy groups, contains at least one 2-halomethyloxyethylene unit, and contains 2,3-dihydroxypropyl end groups (as described). Such halogenated polyether optionally may be provided in the form of an oligomer (as described). The novel compounds when handled are not believed to require the cumbersome worker protection measures which are commonly being utilized when epoxy compounds are employed in similar end uses.

41 Claims, No Drawings

NOVEL POLYETHER CONTAINING AT LEAST ONE 2-HALOMETHYLOXYETHYLENE UNIT AND 2,3-DIHYDROXYPROPYL END GROUPS

CROSS-REFERENCE TO RELATED APPLICATION

In U.S. Ser. No. 344,724, filed Apr. 28, 1989, of Norman S. Anderson and Albert L. Promislow entitled "Organic Polymers Having a Modified Surface and Process Therefor" is described as a generically defined invention wherein the surfaces of organic articles are modified by a reaction product which in preferred embodiments may employ during its formation the novel halogenated polyether of the present invention.

BACKGROUND OF THE INVENTION

Heretofore it commonly has been a practice to initially activate a polymeric surface prior to bonding the same to an elastomeric material. For instance, the surfaces of polyethylene terephthalate tire cords commonly are treated so that they will better adhere to the rubber of a tire.

It has been a common practice to use reactive epoxy compounds during the activation of the polymeric surface. Such epoxy compounds are commercially available in which the epoxide groups are preformed and provide an essential component of the molecule. See, for instance, U.S. Pat. Nos. 3,793,425 and 4,044,189 to Robert J. Arrowsmith. Alternatively, one may select an epichlorohydrin ether or ester derived from a polyhydric alcohol or polycarboxylic acid, such as disclosed in U.S. Pat. No. 4,438,178 to Edward J. Powers. However, when this approach is selected, the active ingredient inherently will form a substantial concentration of epoxide groups during use. It has also been proposed in the past to use homopolymers of epichlorohydrin in some adhesive applications.

It is well recognized by those skilled in this technology that any material which is used to activate a polymeric surface should not unduly interfere with the processing and handling of the polymeric material. For instance, it is important that adhesive activated polymeric tire cords be capable of being handled and readily pass through the requisite equipment in the absence of undue adhesion to objects with which they come in contact. Accordingly, such adhesion promoters must be capable of forming an adhesive-activated product which well provides the required adhesion promotion, requisite solubility for ease of application, the absence of excessive tackiness which will interfere with the handling and processing of the surface-activated product, and the absence of excessive buildup of the adhesion promoter on the processing equipment.

In recent years health concerns have been raised with respect to the use of various adhesion-promoting systems of the prior art which rely upon the use of epoxide groups to facilitate the desired adhesion. It is understood that extensive medical testing has indicated that prolonged exposure to very high levels of the adhesion-promoting epoxy compounds can produce adverse health effects in laboratory animals. It further is understood that the testing to date has indicated no human health effects which can be attributed to the adhesion-promoting epoxy compounds. Nevertheless, it has often become a standard practice to adopt worker health-protection measures for the safety of those who may come in contact with the adhesion-promoting epoxy compounds. These have included, the wearing of special clothing, the use of air-filtration masks by workers, the requirement for workers to shower at the conclusion of a work shift, etc.

It is an object of the invention to provide a novel halogenated polyether which is substantially free of epoxy groups.

It is an object of the present invention to provide a novel polyether containing at least one 2-halomethyloxyethylene unit and 2,3-dihydroxypropyl end groups in the substantial absence of epoxy groups (as described).

It is another object of the present invention to provide a novel halogenated polyether which has been found to possess the requisite characteristics for satisfactory service as a promoter of adhesion between a polymeric surface and an elastomeric material.

It is another object of the present invention to provide a novel halogenated polyether which while substantially lacking epoxy groups surprisingly has been found to make possible good adhesion and good processability in the resulting product when used as a promoter of adhesion between a polymeric surface and an elastomeric material.

It is a further object of the present invention to provide a novel halogenated polyether which is believed to be suitable for handling by workers without the need for cumbersome protection measures.

These and other objects and advantages of the present invention will be apparent to those skilled in the art from the following detailed description and appended claims.

SUMMARY OF THE INVENTION

A halogenated polyether is provided containing at least one 2-halomethyloxyethylene unit and 2,3-dihydroxypropyl end groups in the substantial absence of epoxy groups which exhibits the following structural formula:

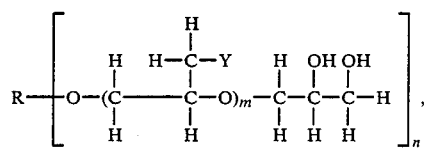

where R is the residual portion of an etherified organic polyhydroxy compound; n is 2 to 8 and designates the number of ether chains extending from R; m is 0 to 7 and designates the number of the illustrated Y-substituted methyloxyethylene units present in each ether chain; Y is selected from the group consisting of hydroxy, chlorine, bromine, iodine, and mixtures of the foregoing; the sum of all of the illustrated Y-substituted methyloxyethylene units in the overall molecule is 1 to 25; and Y must be chlorine, bromine, and/or iodine in at least a portion of the overall molecule, with the proviso that when bromine and iodine are absent in Y there must be at least two 2-chloromethyloxyethylene units in the overall molecule, and when bromine or iodine are present in Y there must be at least one 2-bromomethyloxyethylene or 2-iodomethyloxyethylene unit in the overall molecule.

As discussed hereafter, in a preferred embodiment the organic polyhydroxy compound is glycerol (i.e., 1,2,3-trihydroxypropane).

DESCRIPTION OF PREFERRED EMBODIMENTS

The halogenated polyether of the present invention, as described in detail hereafter, may be formed by (1) the reaction of an organic polyhydroxy compound with epihalohydrin to create ether linkages, (2) the epoxidation of the ends of the ether chains which extend from the residual portion of the organic polyhydroxy compound, and (3) the substantial hydrolysis of the epoxy groups. It should be understood, however, that it is not essential that the halogenated polyether of the present invention be formed by the preferred synthesis route which is described herein.

The organic polyhydroxy compound which may serve as the starting material commonly will possess 2 to 8 hydroxyl groups (e.g., 2 to 6 hydroxyl groups) and be free of other reactive groups which would otherwise interfere with the synthesis reaction described hereafter. However, for some end use applications it may be desirable to select an organic polyhydroxy compound containing an even greater number of hydroxyl groups per molecule.

Representative organic polyhydroxy compounds which may be selected to serve as the starting material include glycerol, ethylene glycol, pentaerythritol, 1,2-propylene glycol, 1,4-butanediol, 1,4-butenediol, trimethylolpropane, sorbitol, mannitol, triethanolamine, thiodiglycol, polyethylene glycol, diglycerol, triglycerol, decaglyerol, neopentylglycol, sorbitan, trimethylolethane, bisphenol A, dipentaerythritol, tripentaerythritol, etc. Preferred polyethylene glycols commonly have molecular weights ranging from approximately 150 to 3,350. The preferred organic polyhydroxy compounds which may serve as starting materials are glycerol, ethylene glycol, polyethylene glycol, and trimethylolpropane. Particularly good results are achieved when the organic polyhydroxy starting material is glycerol (i.e., 1,2,3-trihydroxypropane).

The organic polyhydroxy compound initially may be caused to undergo etherification by reaction with epihalohydrin of the formula:

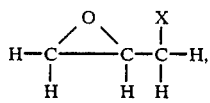

where X is chlorine, bromine, iodine, or mixtures of these, in the presence of an appropriate catalyst. Accordingly, suitable epihalohydrins are epichlorohydrin, epibromohydrin, and epiiodohydrin. The preferred epihalohydrin is epichlorohydrin. Suitable acid catalysts for the etherification reaction are Lewis acids, such as BF$_3$, stannic chloride, organotitanates, etc.; organo acids, such as para-toluene sulfonic acid, methane sulfonic acid, etc.; and inorganic acids, such as sulfuric acid. Particularly good results are achieved when utilizing BF$_3$ as the catalyst in a concentration of approximately 0.02 to 0.2 percent by weight based on the weight of the reactants.

The initial reaction of the polyhydroxy compound with epihalohydrin may be illustrated by the following equation:

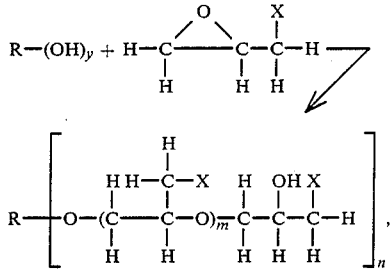

where y equals the number of hydroxyl groups present in the organic polyhydroxy compound wherein the remaining portion of the molecule of the polyhydroxy compound is designated R; X is chlorine, bromine, iodine, or mixtures of these; n is 2 to 8 and designates the number of ether chains extending from R; m is 0 to 7 and designates the number of the illustrated chlorine, bromine or iodine-substituted methyloxyethylene units present in each ether chain; the sum of all of the illustrated chlorine, bromine, and iodine-substituted methyloxyethylene units in the overall molecule is 1 to 25 with the proviso that when bromine and iodine are absent in X there must be at least two 2-chloromethyloxyethylene units in the overall molecule following etherification, and when bromine or iodine are present in X there must be at least one 2-bromomethyloxyethylene or 2-iodomethyloxyethylene unit in the overall molecule following etherification. The number of moles of epihalohydrin which react with each mole of the polyhydroxy compound may be varied in order to yield the desired product. Generally the number of moles of epihalohydrin which react with each mole of the polyhydroxy compound equals the sum of all the chlorine, bromine, and iodine-substituted methyloxyethylene units in the ether chains of the overall molecule plus the number of ether chains extending from the polyhydroxy compound.

Each ether chain following etherification preferably contains 0 to 5, and most preferably 0 to 3 chlorine, bromine, iodine-substituted methyloxyethylene units, and the sum of all of the illustrated chlorine, bromine, and iodine-substituted methyloxyethylene units in the overall molecule preferably is 1 to 15 subject to the previously stated proviso with respect to the nature of the halogen, and most preferably is 2 to 8 (e.g., 2 to 5 or 3 to 5). Should subsequent reaction conditions be selected which result in the conversion of a portion of the chlorine, bromine and/or iodine substitution to hydroxy groups, then in at least some instances the concentration of chlorine, bromine, and/or iodine-substituted methyloxyethylene units advantageously may be incorporated in a greater quantity during the initial etherification.

During the etherification the epihalohydrin reacts directly with the hydroxy groups of the organic polyhydroxy compound and forms 2-halomethyloxyethylene units within the ether chains which extend from the residual portion of the organic polyhydroxy compound. The primary hydroxy groups of the organic polyhydroxy compound tend to first undergo reaction with the epihalohydrin. Any secondary hydroxyl groups of the organic polyhydroxy compound exhibit a lesser propensity to undergo reaction with the epihalohydrin. It is not essential that all of the hydroxyl groups of the organic polyhydroxy compound undergo reaction to form the illustrated ether chains extending from R provided at least two of the hydroxy groups are etherified. In a preferred embodiment all of the hydroxy groups of the polyhydroxy compound are etherified.

The product of the etherification reaction next may be caused to undergo a reaction wherein the ends of the chains which extend from the residual portion of the organic polyhydroxy compound are converted to an epoxide. Such epoxidation may be carried out in the presence of a base at ambient conditions. A preferred base for use in the epoxidation reaction is sodium hydroxide. When sodium hydroxide serves as the base, water and sodium chloride are formed as byproducts. Other representative bases which similarly may be utilized include potassium hydroxide, magnesium hydroxide, calcium hydroxide, lithium hydroxide, sodium carbonate, potassium carbonate, calcium carbonate, magnesium carbonate, etc. Commonly the number of moles of base employed per mole of etherified product corresponds to the number of ether side chains which extend from the residual portion of the organic polyhydroxy compound. If the epoxidation conditions are more severe (e.g., higher base concentrations and/or elevated temperatures), a portion of chlorine, bromine, and iodine-substituted methyloxyethylene units will be converted to hydroxy-substituted methyloxyethylene units. At the conclusion of the epoxidation reaction an intermediate product of the following formula commonly is formed:

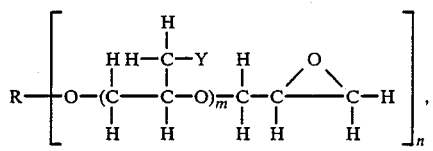

where Y is hydroxy, chlorine, bromine, iodine, and mixtures of two or more of these, and m and n are as previously described.

Finally, the above-identified intermediate may be caused to undergo an hydrolysis reaction in which the epoxy groups are substantially eliminated to form the novel halogenated polyether of the present invention. The hydrolysis reaction commonly is carried out in the presence of an acid at a temperature of approximately 50° to 40° C. For instance, sulfuric acid may be utilized when present in a concentration of 0.05 to 0.2 percent by weight based on the weight of the reactants. Other representative hydrolysis media which may be selected include perchloric acid, para-toluene sulfonic acid, methane sulfonic acid, etc.

The more severe hydrolysis conditions may further result in a portion of the chlorine, bromine, and iodine-substituted methyloxyethylene units being converted to hydroxy-substituted methyloxyethylene units. Also, the hydrolysis reaction may optionally be practiced under conditions where oligomerization (i.e., formation of dimers, trimers, tetramers, etc.) is promoted through the reaction of the first formed 2,3-dihydroxypropyl end groups with unreacted epoxy groups to form higher molecular weight compounds having ether linkages. Such oligomer formation is promoted when the reactions are not vigorously mixed during the course of the hydrolysis.

The resulting product may be washed with water to remove impurities and byproducts of the reaction, and the water and other volatile materials subsequently removed by stripping.

At the conclusion of the hydrolysis reaction the resulting halogenated polyether contains at least one 2-halomethyloxyethylene unit and 2,3-dihydroxypropyl end groups in the substantial absence of epoxy groups and exhibits the following structural formula:

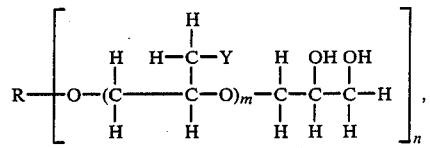

where R is the residual portion of an etherified organic polyhydroxy compound; n is 2 to 8 and designates the number of ether chains extending from R; m is 0 to 7 (e.g., 0 to 5 to 3) and designates the number of the illustrated Y-substituted methyloxyethylene units present in each ether chain; Y is selected from the group consisting of hydroxy, chlorine, bromine, iodine, and mixtures of the foregoing; the sum of all of the illustrated Y-substituted methyloxyethylene units in the overall molecule is 1 to 25 (e.g., 1 to 15 or 2 to 8); and Y must be chlorine, bromine, and/or iodine in at least a portion of the overall molecule, with the proviso that when bromine and iodine are absent in Y there must be at least two 2-chloromethyloxyethylene units in the overall molecule, and when bromine or iodine are present in Y there must be at least one 2-bromomethyloxyethylene or 2-iodomethyloxyethylene unit in the overall molecule. As previously indicated, it is not essential that all of the hydroxyl groups present on R be etherified.

A halogenated polyether oligomer having a structure which corresponds to that of a plurality of molecules of the halogenated polyether previously illustrated optionally may be formed during the hydrolysis step as previously discussed wherein at least two of the illustrated 2,3-dihydroxypropyl end groups of the ether chains of different molecules are chemically combined through an ether linkage with the absence of the illustrated 3-hydroxy portion of the 2,3-dihydroxypropyl end groups, and at least two of the illustrated ether chains of the resulting oligomer having 2,3-dihydroxypropyl end groups remain intact.

In a preferred embodiment, the halogenated polyether of the present invention is formed while using glycerol as the organic polyhydroxy compound, contains at least one 2-halomethyloxyethylene unit and 2,3-dihydroxypropyl end groups in the substantial absence of epoxy groups and exhibits the following structural formula:

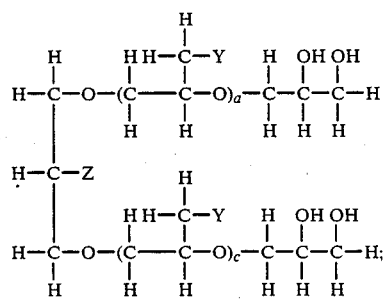

Where Z is selected from the group consisting of OH, and

-continued

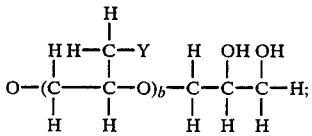

a, b, and c designate the number of the illustrated Y-substituted methyloxyethylene units present in each ether chain; Y is selected from the group consisting of hydroxy, chlorine, bromine, iodine, and mixtures thereof; a is 1 to 3; b is 0 to 2; c is 0 to 3 (e.g., 1 to 3); and a+b+c is 2 to 5 (e.g., 3 or 4); and Y must be chlorine, bromine, and/or iodine in at least a portion of the overall molecule, with the proviso that when bromine and iodine are absent in Y there must be at least two 2-chloromethyloxyethylene units in the overall molecule, and when bromine or iodine are present in Y there must be at least one 2-bromomethyloxyethylene or 2-iodomethyloxyethylene unit in the overall molecule.

In a particularly preferred embodiment the halogenated polyether of the present invention contains at least three 2-chloromethyloxyethylene units and 2,3-dihydroxypropyl end groups in the substantial absence of epoxy groups and exhibits the following structural formula:

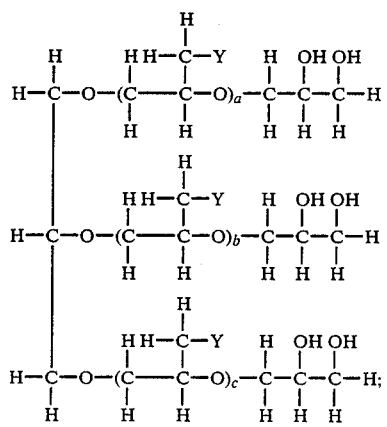

where Y is selected from the group consisting of hydroxy, chlorine, and mixtures of hydroxy and chlorine; a, b, and c designate the number of the illustrated Y-substituted methyloxyethylene units present in each ether chain; a is 1 to 3; b is 0 to 2; c is 1 to 3; and a+b+c is 3 to 5 (e.g., 4); and Y must be chlorine in at least a portion of the overall molecule, with the proviso that there must be at least three 2-chloromethyloxyethylene units in the overall molecule.

It should be understood that one may optionally include other comonomer units in the resulting halogenated polyether of the present invention so long as such moieties do not unduly diminish the usefulness of the molecules during the essential recurring units as illustrated. Representative comonomer units are derived from ethylene oxide, propylene oxide, butylene oxide, glycidol, etc.

The novel halogenated polyethers of the present invention commonly are liquids at room temperature. The halogenated polyethers of the present invention commonly exhibit at least some solubility in water at 25° C. Some are completely soluble. Others exhibit less than complete solubility and can be emulsified into an aqueous medium with emulsifiers, or dissolved in organic solvents or carriers. The solubility in water tends to decrease with increasing quantities of the substituted methyloxyethylene units which include chlorine, bromine or iodine. Hydroxyl values of approximately 20 to 700 (e.g., 100 to 700) mg.KOH/g. frequently are exhibited, as well as organic halogen contents of approximately 3 to 60 percent by weight (e.g., approximately 14 to 40 percent by weight). The hydroxyl values may be determined by the standard pyridine/acetic anhydride method. The organic halogen values are determined by substracting ionic halogen from total halogen with both being measured by use of a microcoulometer.

In preferred embodiments the epoxy and halohydrin values in the final product are extremely low. For instance, the product preferably contains no more than 0.5 percent of epoxy groups by weight, and most preferably no more than 0.2 percent of epoxy groups by weight. The epoxy content of the product may conveniently be determined by titration of the dry product with perchloric acid in the presence of tetraethylammonium bromide. See, also ASTM D-1652-73 as modified by the publication of Shell Chemicals entitled "Determination of α-Epoxy Group in EPON Resins". Also, the bound halohydrin content within the product as percent chlorine preferably should be less than 0.5, and most preferably less than 0.25. The halohydrin content of the product may conveniently be determined by consumption of 0.5N. sodium hydroxide by the product over 30 minutes at room temperature after adjusting for any activity in the sample.

The nature of the ether chains extending from the residual portion of the etherified organic polyhydroxy compound may be analyzed by use of carbon 13 NMR in accordance with known analytical techniques.

The halogenated polyether of the present invention has been found to be particularly useful as a promoter of good adhesion between a polymeric surface and an elastomeric material and may be substituted with advantage for various epoxy compounds which heretofore commonly have served this role. See, U.S. patent application Ser. No. 344724, filed Apr. 28, 1989, of Norman S. Anderson and Albert L. Promislow entitled "Organic Polymers Having a Modified Surface and Process Therefor", which is herein incorporated by reference, for a further discussion of how the halogenated polyethers of the present invention may be put to this end use.

The adhesion of polymeric materials, such as polyesters (e.g., polyethylene terephthalate), aromatic polyamides (e.g., polyparaphenylene terephthalamide, polymetaphenylene isophthamide, etc.), and graphitic polymers to elastomeric materials (e.g. rubber) is particularly amenable to enhancement through the use of the halogenated polyether of the present invention. Other polymers which likewise will benefit are nylons, polyketones, polyetherketones, polyethylenes, polyphenylene sulfides, polyvinyl alcohols, etc. The polymeric material can be provided in a variety of configurations, such as fibers, films, sheets, rods, etc. The halogenated polyether is particularly useful when applied to fibers, yarns, or cords which serve as reinforcement in pneumatic tires.

When employed in an adhesion-promoting application, the halogenated polyether may be applied as an emulsion (e.g., an aqueous emulsion) or as a solution together with a coreactant to the polymeric surface which is undergoing treatment. When treating fibers, the halogenated polyether may conveniently be applied together with the coreactant (1) immediately after fiber spinning and prior to drawing, or (2) following drawing. The halogenated polyether and coreactant preferably are applied to the organic polymer surface and heated to an elevated temperature at least 100° C. whereon a reaction occurs to produce a polyether and an inorganic halide in the polymer surface to bring about the desired modification.

Preferred coreactants for use with the halogenated polyether are quaternary ammonium and alkali metal hydroxides, bicarbonates, carbonates, formates, and acetates. These compounds, optionally can be buffered to an acidic pH with a volatile acid, such as carbonic, acetic, and propionic acids. The coreactant as applied generally comprises at least 0.002 cation equivalent per 10 grams of halogenated polyether and preferably at least 0.005 cation equivalent. When polyethylene terephthalate filamentary material is surface modified, the fibers commonly will bear from 0.01 to 0.1 percent by weight of the halogenated polyether and coreactant based upon the weight of the filamentary material.

When it is desired to use the surface-modified polyethylene terephthalate filamentary material in the production of a tire, typically a resorcinol-formaldehyde-resin and a rubber latex such as a styrene-butadiene vinyl pyridine latex (e.g., an RFL composition) also will be applied in a concentration of approximately 2 to 10 percent by weight based upon the weight of the filamentary material.

It is noteworthy that the halogenated polyethers may be substituted for adhesion promoters of the prior art which heavily rely upon their epoxy functionality to bring about the desired adhesion promotion. The substantial absence of epoxy groups in the halogenated polyethers of the present invention accordingly, is believed to eliminate the need for cumbersome worker protection measures which are commonly being practiced. A more pleasant and healthful workplace is thereby facilitated through the use of the improved compounds of the present invention.

The following examples are presented as specific illustrations of the claimed invention. It should be understood, however, that the invention is not limited to the specific details set forth in the examples.

EXAMPLE I 426.6 grams of glycerol initially are caused to react with 3,000 grams of epichlorohydrin in the presence of 13.7 grams of 12 percent active boron trifluoride-methanol complex which serve as a catalyst. The molar ratio of epichlorohydrin to glycerol is 7:1. The reaction is carried out at a temperature of 40° to 60° C. while present in a glass reaction vessel equipped with a reflux condenser and external cooling bath. The glycerol and catalyst are premixed and the epichlorohydrin is slowly charged to help control the exotherm. During the course of this reaction the etherification of hydroxyl groups of the glycerol takes place and ether chains are formed which extend from the residual portion of the glycerol and include 2-chloromethyloxyethylene units together with 2-hydroxy-3-chloropropyl end groups. On average there are four 2-chloromethyloxyethylene units per overall molecule which are primarily incorporated in the two chains resulting from the etherification of the primary hydroxy groups of the glycerol.

Following etherification 1,500 grams of the intermediate product are diluted with 375.1 grams of methyl isobutyl ketone and are subjected to an expoxidation reaction with 608.2 grams of a 50 percent sodium hydroxide aqueous solution. The reaction is carried out at a temperature of 25° to 40° C. while agitated in a reaction vessel for one hour. The contents of the reaction vessel are allowed to stand for one hour to permit the mixture to separate into two phases. The upper phase contains primarily the resulting epoxide, any unreacted epichlorohydrin, and methyl isobutyl ketone. The lower phase contains primarily water, sodium hydroxide, and sodium chloride byproduct and is discarded. The upper phase next is mixed for one hour with 147.3 grams of a 50 precent sodium hydroxide aqueous solution and is then allowed to stand for 14 hours which again permits the mixture to separate into two phases. The upper phase is removed by decantation and the lower phase is discarded. The upper phase is filtered using Whattman No. 4 filter paper in order to remove any residual sodium chloride. The filtered product of the epoxidation next is placed in a reaction flask where it is heated at 90° to 110° C. under a 10 mm. vacuum to remove the methyl isobutyl ketone. During the course of the epoxidation reaction the 2-hydroxy-3-chloropropyl end groups are substantially all converted to epoxy groups and the 2-chloromethyloxyethylene units remain substantially intact.

Following epoxidation 400 grams of the intermediate product next are subjected to an hydrolysis reaction to form the halogenated polyether product of the present invention. More specifically, the pH of 600 ml. of water is adjusted to a value of 2.0 by the addition of 0.4 gram of 98 percent sulfuric acid to form the hydrolysis medium. The temperature of the hydrolysis medium while present in a glass reaction vessel is raised to approximately 75° C. and is placed under strong agitation by means of mechanical agitation. The hydrolysis reaction is initiated by gradually adding the intermediate product formed by epoxidation to the hydrolysis medium with stirring. The resulting mixture next is maintained with agitation at approximately 85° C. for an additional 18 hours. During the course of the hydrolysis reaction the epoxy end groups are substantially all converted to 2,3-dihydroxypropyl end groups. There is substantially no oligomerization under these hydrolysis conditions. The 2-chloromethyloxyethylene units remain substantially intact during the hydrolysis reaction. The mixture next is neutralized by adding 10 grams of 30 percent sodium carbonate aqueous solution to raise the pH to a value of approximately 4.5. The resulting aqueous dispersion is next placed under a vacuum of 10 mm. and the water is stripped away.

The resulting product of the present invention contains both primary chlorine groups and primary hydroxyl groups. These are situated upon the molecule at locations which preclude the formation of epoxy groups during subsequent use. The molecules of the product contain an average four 2-chloromethyloxyethylene units with these being located primarily upon the chains resulting from the etherification of the primary hydroxyl groups of the glycerol. The product could be termed a glycerol ether containing nominally four 2-chloromethyloxyethylene units with terminal 1-glycerol ether units or a polyoxychloropropylene glycerol with terminal 1-glycerol ethers. At room temperature the product is a liquid, exhibits slight solubility in water at 25° C., exhibits a hydroxyl value of 501 mg.KOH/g., an organic chloride content of 18.5 percent by weight, an epoxy value of 0.03 percent by weight, and a chlorohydrin value which is less than 0.25 percent by weight as chlorine. The resulting halogenated polyether product has been demonstrated to be well suited for use as a promoter of good adhesion between a polymeric surface and an elastomeric material as previously described.

EXAMPLE II

Example I is substantially repeated with the exception that 3,000 grams of epichlorohydrin initially are reacted with 597.6 grams of glycerol. The molar ratio of epichlorohydrin to glycerol is 5:1.

At the conclusion of the etherification reaction 1,000 grams of the intermediate product are diluted with 250.1 grams of methyl isobutyl ketone and are initially subjected to the epoxidation reaction with 541.2 grams of a 50 percent sodium hydroxide aqueous solution. The upper phase subsequently is mixed with 106.3 grams of a 50 percent sodium hydroxide aqueous solution.

The molecules of the final product contain an average two 2-chloromethyloxyethylene units with these being located primarily on the chains resulting from the etherification of the primary hydroxyl groups of the glycerol. At room temperature the product is a liquid, exhibits fair solubility in water at 25° C., exhibits a hydroxyl value of 575 mg.KOH/g., an organic chloride content of 13.7 percent by weight, an epoxy weight of 0.04 percent by weight, and a chlorohydrin content of 0.42 percent by weight as chlorine.

EXAMPLE III

Example I is substantially repeated with the exception that ethylene glycol is selected as the organic polyhydroxy starting material and 3,000 grams of epichlorohydrin initially are reacted with 502.6 grams of the ethylene glycol. The molar ratio of epichlorohydrin to ethylene glycol is 4:1.

At the conclusion of the etherification reaction 2,335.2 grams of the intermediate product are diluted with 583.6 grams of methyl isobutyl ketone and are initially subjected to the epoxidation reaction with 1,081.2 grams of a 50 percent sodium hydroxide aqueous solution. The upper phase subsequently is mixed with 233 grams of a 50 percent sodium hydroxide aqueous solution.

The molecules of the final product contain on average two 2-chloromethyloxyethylene units in the chains of the overall molecule resulting from the etherification together with 2,3-dihydroxypropyl end groups. At room temperature the product is a liquid, exhibits good solubility in water at 25° C., exhibits a hydroxyl value of 533 mg.KOH/g., an organic chloride content of approximately 18.3 percent by weight, an epoxy value of 0.24 percent by weight, and a chlorohydrin content of 0.23 percent by weight as chlorine.

EXAMPLE IV

Example I is substantially repeated with the exception that trimethylolpropane is selected as the organic polyhydroxy starting material. 2,000 grams of epichlorohydrin initially are reacted with 414 grams of the trimethylolpropane. The molar ratio of epichlorohydrin to trimethylolpropane is 7:1.

At the conclusion of the etherification reaction 1,000.2 grams of the intermediate product are diluted with 249.8 grams of methyl isobutyl ketone and initially are subjected to the epoxidation reaction with 383.8 grams of a 50 percent sodium hydroxide aqueous solution. The upper phase subsequently is mixed with 200 grams of a 50 percent sodium hydroxide aqueous solution.

The molecules of the final product contain an average four 2-chloromethyloxyethylene units in the chains of the overall molecule resulting from the etherification together with 2,3-dihydroxypropyl end groups. At room temperature the product is a liquid, exhibits low solubility in water at 25° C., exhibits a hydroxyl value of 450 mg.KOH/g., an organic chloride content of approximately 22.6 percent by weight, an epoxy value of 0.2 percent by weight, and a chlorohydrin content of 0.21 percent by weight as chlorine.

EXAMPLE V

Example I is substantially repeated with the exception that glycerol is selected as the polyhydroxy starting material and 1,000 grams of epibromohydrin are reacted with 134.4 grams of glycerol at a temperature of 85° C. The molar ratio of epibromohydrin to glycerol is 5:1.

At the conclusion of the etherification reaction 1,104.3 grams of the intermediate product are diluted with 276.1 grams of methyl isobutyl ketone and initially are subjected to the epoxidation reaction with 426.4 grams of a 50 percent sodium hydroxide aqueous solution. The upper phase subsequently is mixed with 60.0 grams of a 50 percent sodium hydroxide aqueous solution.

The final product is primarily a dimer formed by the combination of two etherified glycerol molecules wherein one 2,3-dihydroxypropyl end group from one molecule reacts with the epoxide of another molecule during the hydrolysis reaction to join the molecules through an ether linkage, and the resulting dimer contains on average approximately two and one-half 2-bromoethyloxyethylene units and approximately one 2-hydroxymethyloxyethylene unit together with uncombined 2,3-dihydroxypropyl end groups. At room temperature the product is a liquid, exhibits a very low solubility in water at 25° C., exhibits a hydroxyl value of 452 mg.KOH/g., exhibits a weight average molecular weight of 834, an organic bromine content of approximately 23.1 percent by weight, an epoxy value of 0.02 percent by weight, and a bromohydrin content of 1.7 percent by weight as bromine.

EXAMPLE VI

Example I is substantially repeated with the exception that polyethylene glycol having an average molecular weight of 1,540 is selected as the organic polyhydroxy starting material and 145.3 grams of epichlorohydrin initially are reacted with 604.7 grams of the polyethylene glycol. The molar ratio of epichlorohydrin to polyethylene glycol is 4:1.

At the conclusion of the etherification reaction 407 grams of the intermediate product are initially subjected to the epoxidation reaction at 45° C. in the absence of methyl isobutyl ketone with 45 grams of a 50 percent sodium hydroxide aqueous solution, are filtered, and subsequently are mixed with an additional 5 grams of a 50 percent sodium hydroxide aqueous solution.

The molecules of the final product contain on average two 2-chloromethyloxyethylene units in the chains of the overall molecule resulting from the etherification together with 2,3-dihydroxypropyl end groups. At room temperature the product is a solid, exhibits excellent solubility in water at 25° C., exhibits a hydroxyl value of 105 mg.KOH/g., an organic chloride content of approximately 3.5 percent by weight, an epoxy value of 0.12 percent by weight, and a chlorohydrin content of 0.25 percent by weight as chlorine.

Although the invention have been described with preferred embodiments it is to be understood that variations and modifications may be employed without departing from the concept of the invention as defined in the following claims.

We claim:

1. A halogenated polyether containing at least one 2-halomethyloxyethylene unit and 2,3-dihydroxypropyl end groups in the substantial absence of epoxy groups which exhibits the following structural formula:

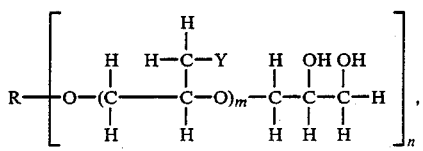

where R is the residual portion of an etherified organic polyhydroxy compound; n is 2 to 8 and designates the number of ether chains extending from R; m is 0 to 7 and designates the number of the illustrated Y-substituted methyloxyethylene units present in each ether chain; Y is selected from the group consisting of hydroxy, chlorine, bromine, iodine, and mixtures of the foregoing; the sum of all of the illustrated Y-substituted methyloxyethylene units in the overall molecule is 1 to 25; and Y must be chlorine, bromine, and/or iodine in at least a portion of the overall molecule, with the proviso that when bromine and iodine are absent in Y there must be at least two 2-chloromethyloxyethylene units in the overall molecule, and when bromine or iodine are present in Y there must be at least one 2-bromoethyloxyethylene or 2-iodomethyloxyethylene unit in the overall molecule.

2. A halogenated polyether according to claim 1 wherein m is 0 to 5 and designates the number of the illustrated Y-substituted methyloxyethylene units present in each ether chain.

3. A halogenated polyether according to claim 1 wherein m is 0 to 3 and designates the number of the illustrated Y-substituted methyloxyethylene units present in each ether claim.

4. A halogenated polyether according to claim 1 wherein the sum of the illustrated Y-substituted methyloxyethylene units in the overall molecule is 1 to 15.

5. A halogenated polyether according to claim 1 wherein the sum of the illustrated Y-substituted methyloxyethylene units in the overall molecule is 2 to 8.

6. A halogenated polyether according to claim 1 wherein all of the hydroxy groups of said organic polyhydroxy compound are etherified.

7. A halogenated polyether according to claim 1 wherein said organic polyhydroxy compound prior to etherification possessed 2 to 8 hydroxyl groups.

8. A halogenated polyether according to claim 1 wherein said organic polyhydroxy compound is selected from the group consisting of glycerol, ethylene glycol, pentaerythritol, 1,2-propylene glycol, 1,4-butanediol 1,4-butenediol, trimethylolpropane, sorbitol, mannitol, triethanolamine, thiodiglycol, polyethylene glycol, diglycerol, triglycerol, decaglycerol, neopentylglycol, sorbitan, trimethylolethane, bispenol A, dipentaerythritol, and tripentaerythritol.

9. A halogenated polyether according to claim 1 wherein said organic polyhydroxy compound is glycerol.

10. A halogenated polyether according to claim 1 wherein said organic polyhydroxy compound is ethylene glycol.

11. A halogenated polyether according to claim 1 wherein said organic polyhydroxy compound is trimethylolpropane.

12. A halogenated polyether according to claim 1 wherein said organic polyhydroxy compound is polyethylene glycol.

13. A halogenated polyether according to claim 1 wherein Y is chlorine.

14. A halogenated polyether according to claim 1 wherein Y is a mixture of hydroxy and chlorine in the overall molecule.

15. A halogenated polyether according to claim 1 wherein Y is bromine.

16. A halogenated polyether according to claim 1 wherein Y is a mixture of hydroxy and bromine in the overall molecule.

17. A halogenated polyether according to claim 1 wherein Y is iodine.

18. A halogenated polyether according to claim 1 wherein Y is a mixture of hydroxy and iodine in the overall molecule.

19. A halogenated polyether according to claim 1 which contains no more than 0.5 percent by weight of epoxy groups.

20. A halogenated polyether according to claim 1 which contains no more than 0.2 percent by weight of epoxy groups.

21. A halogenated polyether oligomer having a structure which corresponds to that of a plurality of molecules of the halogenated polyether of claim 1 wherein at least two of the illustrated 2,3-dihydroxypropyl end groups of the ether chains of different molecules are chemically combined through an ether linkage with the absence of the illustrated 3-hydroxy portion of the 2,3-dihydroxypropyl end groups, and at least two of the illustrated ether chains of the resulting oligomer having 2,3-dihydroxypropyl end groups remain intact.

22. A halogenated polyether containing at least one 2-halomethyloxyethylene unit and 2,3-dihydroxypropyl end groups in the substantial absence of epoxy groups which exhibits the following structural formula:

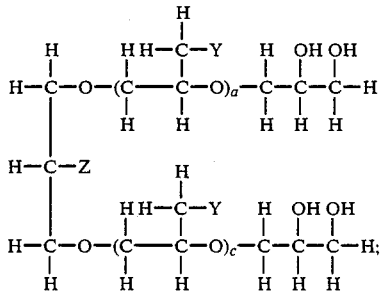

where Z is selected from the group consisting of OH, and

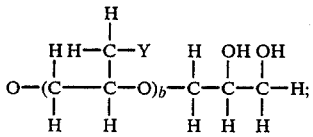

a, b, and c designate the number of the illustrated Y-substituted methyloxyethylene units present in each ether chain; Y is selected from the group consisting of hydroxy, chlorine, bromine, iodine, and mixtures thereof; a is 1 to 3; b is 0 to 2; c is 0 to 3; and a+b+c is 2 to 5; and Y must be chlorine, bromine, and/or iodine in at least a portion of the overall molecule, with the proviso that when bromine and iodine are absent in Y there must be at least two 2-chloromethyloxyethylene units in the overall molecule, and when bromine or iodine are present in Y there must be at least one 2-bromomethyloxyethylene or 2-iodomethyloxyethylene unit in the overall molecule.

23. A halogenated polyether according to claim 22 wherein Y is chlorine.

24. A halogenated polyether according to claim 22 wherein Y is a mixture of hydroxy and chlorine in the overall molecule.

25. A halogenated polyether according to claim 22 wherein Y is bromine.

26. A halogenated polyether according to claim 22 wherein Y is a mixture of hydroxy and bromine in the overall molecule.

27. A halogenated polyether according to claim 22 wherein Y is iodine.

28. A halogenated polyether according to claim 22 wherein Y is a mixture of hydroxy and iodine in the overall molecule.

29. A halogenated polyether according to claim 22 wherein c is 1 to 3.

30. A halogenated polyether according to claim 22 wherein a+b+c is 3.

31. A halogenated polyether according to claim 22 wherein a+b+c is 4.

32. A halogenated polyether according to claim 22 wherein Y is chlorine and a+b+c is 4.

33. A halogenated polyether according to claim 22 which contains no more than 0.5 percent by weight of epoxy groups.

34. A halogenated polyether according to claim 22 which contains no more than 0.2 percent by weight of epoxy groups.

35. A halogenated polyether oligomer having a structure which corresponds to that of a plurality of molecules of the halogenated polyether of claim 22 wherein at least two of the illustrated 2,3-dihydroxypropyl end groups of the ether chains of different molecules are chemically combined through an ether linkage with the absence of the illustrated 3-hydroxy portion of the 2,3-dihydroxypropyl end groups, and at least two of the illustrated ether chains of the resulting oligomer having 2,3-dihydroxypropyl end groups remain intact.

36. A halogenated polyether containing at least three 2-chloromethyloxyethylene units and 2,3-dihydroxypropyl end groups in the substantial absence of epoxy groups which exhibits the following structural formula:

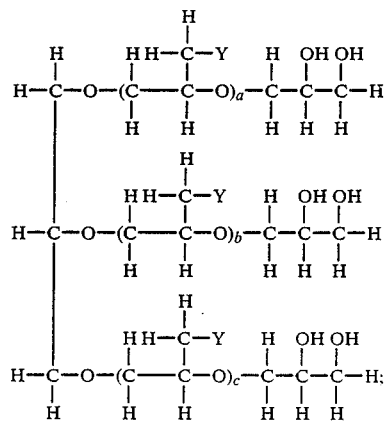

where Y is selected from the group consisting of hydroxy, chlorine, and mixtures of hydroxy and chlorine; a, b, and c designate the number of the illustrated Y-substituted methyloxyethylene units present in each ether chain; a is 1 to 3; b is 0 to 2; c is 1 to 3; and a+b+c is 3 to 5; and Y must be chlorine in at least a portion of the overall molecule, with the proviso that there must be at least three 2-chloromethyloxyethylene units in the overall molecule.

37. A halogenated polyether according to claim 36 wherein a+b+c is 4.

38. A halogenated polyether according to claim 36 wherein Y is chlorine, and a+b+c is 4.

39. A halogenated polyether according to claim 36 which contains no more than 0.5 percent by weight of epoxy groups.

40. A halogenated polyether according to claim 36 which contains no more than 0.2 percent by weight of epoxy groups.

41. A halogenated polyether oligomer having a structure which corresponds to that of a plurality of molecules of the halogenated polyether of claim 36 wherein at least two of the illustrated 2,3-dihydroxypropyl end groups of the ether chains of different molecules are chemically combined through an ether linkage with the absence of the illustrated 3-hydroxy portion of the 2,3-dihydroxypropyl end groups, and at least two of the illustrated ether chains of the resulting oligomer having 2,3-dihydroxypropyl end groups remain intact.

* * * * *